US005234418A

United States Patent [19]

McAnlis

[11] Patent Number: 5,234,418

[45] Date of Patent: Aug. 10, 1993

[54] APPARATUS AND METHOD FOR BATHING AND/OR SOAKING

[76] Inventor: Christine L. McAnlis, 3702 Bates, Irvine, Calif. 92714

[21] Appl. No.: 667,441

[22] Filed: Mar. 11, 1991

[51] Int. Cl.[5] .................. A61M 35/00

[52] U.S. Cl. .................. 604/289; 4/443; 4/619

[58] Field of Search .................. 4/441, 442, 443, 619, 4/621; 604/289, 290, 317; 209/418, 419; 141/333, 317, 334, 339; 138/40, 41, 42

[56] References Cited

U.S. PATENT DOCUMENTS 612,433 10/1898 Orford .

2,812,784 11/1957 Palmer .................. 141/333

3,109,459 6/1962 Lee et al. .................. 138/41

3,255,570 6/1966 Weimer .................. 141/108

3,680,547 8/1972 Higgs .................. 128/66

3,770,200 11/1973 Bauer et al. .................. 239/102

4,326,308 4/1982 Silver .................. 4/445

*Primary Examiner*—Randall L. Green

*Assistant Examiner*—R. Clarke

*Attorney, Agent, or Firm*—Richard L. Gausewitz

[57] ABSTRACT

A method of bathing and soaking the perineum of women, including postpartum women, by standing in the shower and directing water from the shown head into an open-topped vessel held between the upper-inner thighs. The related apparatus incorporates dam means to assure that excessive water velocities do not occur.

14 Claims, 2 Drawing Sheets

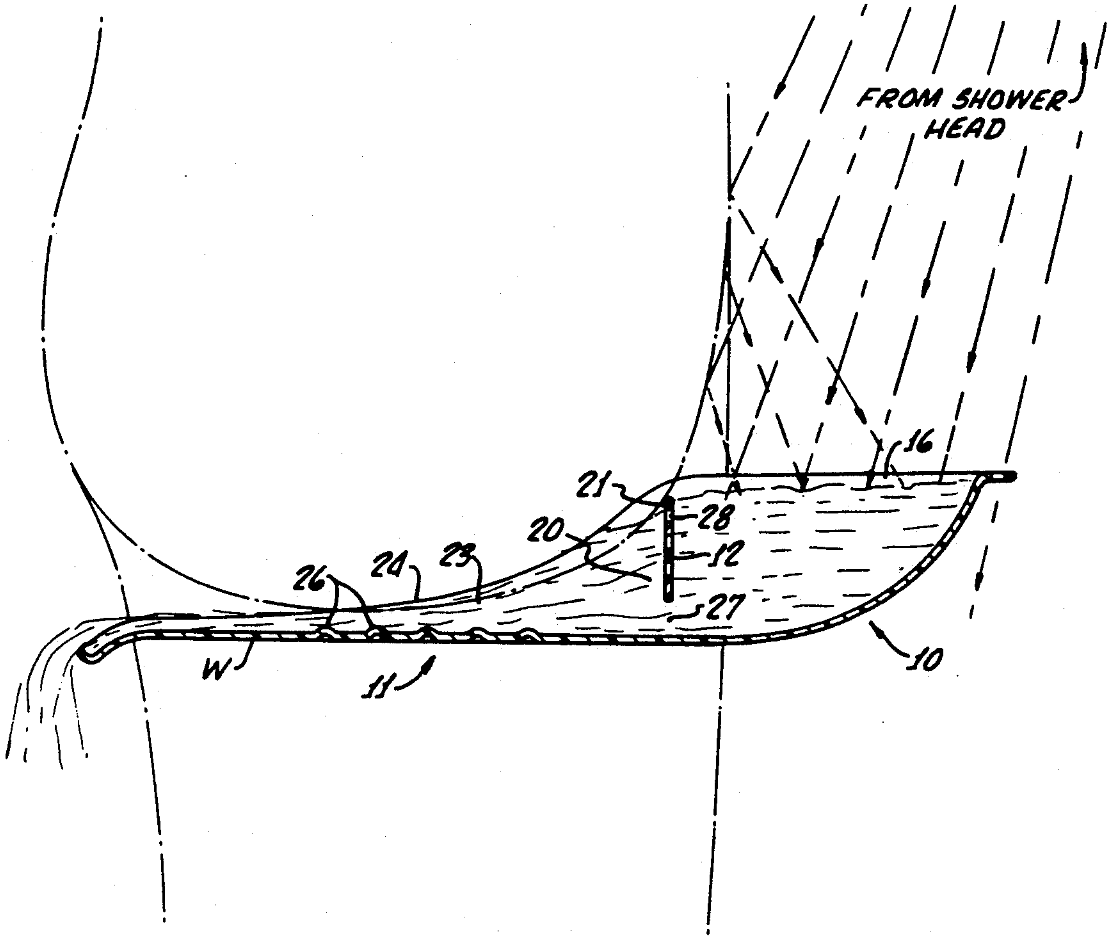
FIG. 1.
FIG. 2.
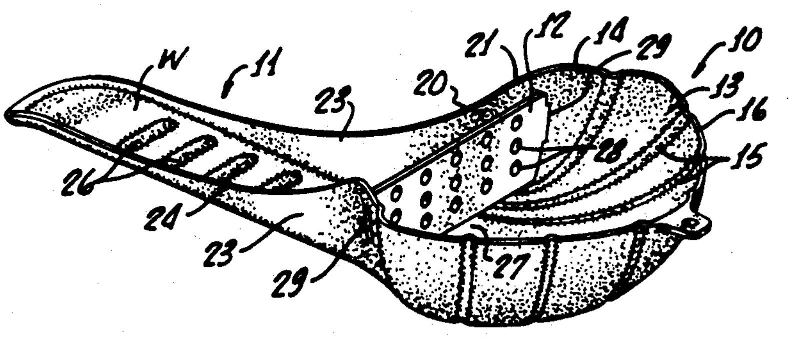

APPARATUS AND METHOD FOR BATHING AND/OR SOAKING

BACKGROUND OF THE INVENTION

Postpartum vaginal-delivery mothers are often directed to take sitz baths, to promote healing of their episiotomy wounds and to reduce the pain of stitches. In the opinion of applicant, however, sitz baths are infrequently taken and——furthermore——are not totally satisfactory when they are taken. For one thing, sitz baths require that the mother sit on a hard surface, either the bottom of a bathtub or the bottom of a relatively large vessel, and this is uncomfortable or painful. Relative to a bathtub, the bottom wall is very difficult to maintain sanitary. In addition, sitz baths to not conventionally have the front-to-back water movement that is important in preventing contamination of the water that contacts the genital regions.

On the other hand, applicant has conceived that there should not be spraying of water, as from a hose, onto the genitals or perineum, especially because the cervix often remains partly dilated and is particularly susceptible to being infected.

There is needed a device and method that will increase blood circulation in response to the stimulation of moving water and in response to the heat of the water; that will decrease the chances of infection by achieving effective cleansing and by maintaining front-to-back water flow; that is very easy to use and therefore will actually be used my the mother or patient; that increases healing time by warming the area and achieving an in-shower soaking action without excessive water flow; that decreases pain and provides a soothing effect by stimulating injured tissues with warm water; that is easily washable and reusable and is inexpensive; and that decreases the chances of infection and increases comfort by keeping new mothers off the bottom of a bathtub.

SUMMARY OF THE INVENTION

Stated generally, the present apparatus comprises an open vessel adapted to receive water as from a shower head, and which communicates with an open channel sized to fit adjacent the genitals and perineum of a woman. In accordance with another aspect of the invention, a partial dam is provided between the open vessel and the open channel to reduce and control the velocity of water flow through the channel. In accordance with another aspect of the invention, the channel is provided with means to elevate the water at spaced points so as to augment the cleansing and therapeutic actions.

In accordance with the method, an open vessel is disposed adjacent the lower torso, water is introduced into the vessel, and water is withdrawn from the vessel and passed adjacent and in contact with the perineum.

In accordance with another aspect of the invention, the introduction of water into the vessel and the withdrawal of water therefrom are simultaneous. In accordance with another aspect, the rate of flow of water is reduced from the rate it would have if there were uncontrolled flow from the vessel to the perineum. In accordance with another aspect, the direction of flow is from the front side of a woman the toward the rear side thereof.

In accordance with another aspect of the invention, water is delivered to the vessel through the air from a shower head while the woman is standing in a shower. In accordance with another aspect, additional water is delivered to the vessel by so locating the arms on the torso that water flows convergently down the torso and into the vessel. In accordance with another aspect, the method is performed relative to a postpartum vaginal-delivery mother.

BRIEF DESCRIPTION OF THE DRAWINGS

FIG. 1 is a vertical longitudinal sectional view of the apparatus as related to a woman;

FIG. 2 is an isometric view of the apparatus;

DETAILED DESCRIPTION OF THE PREFERRED EMBODIMENT

Figure 3:
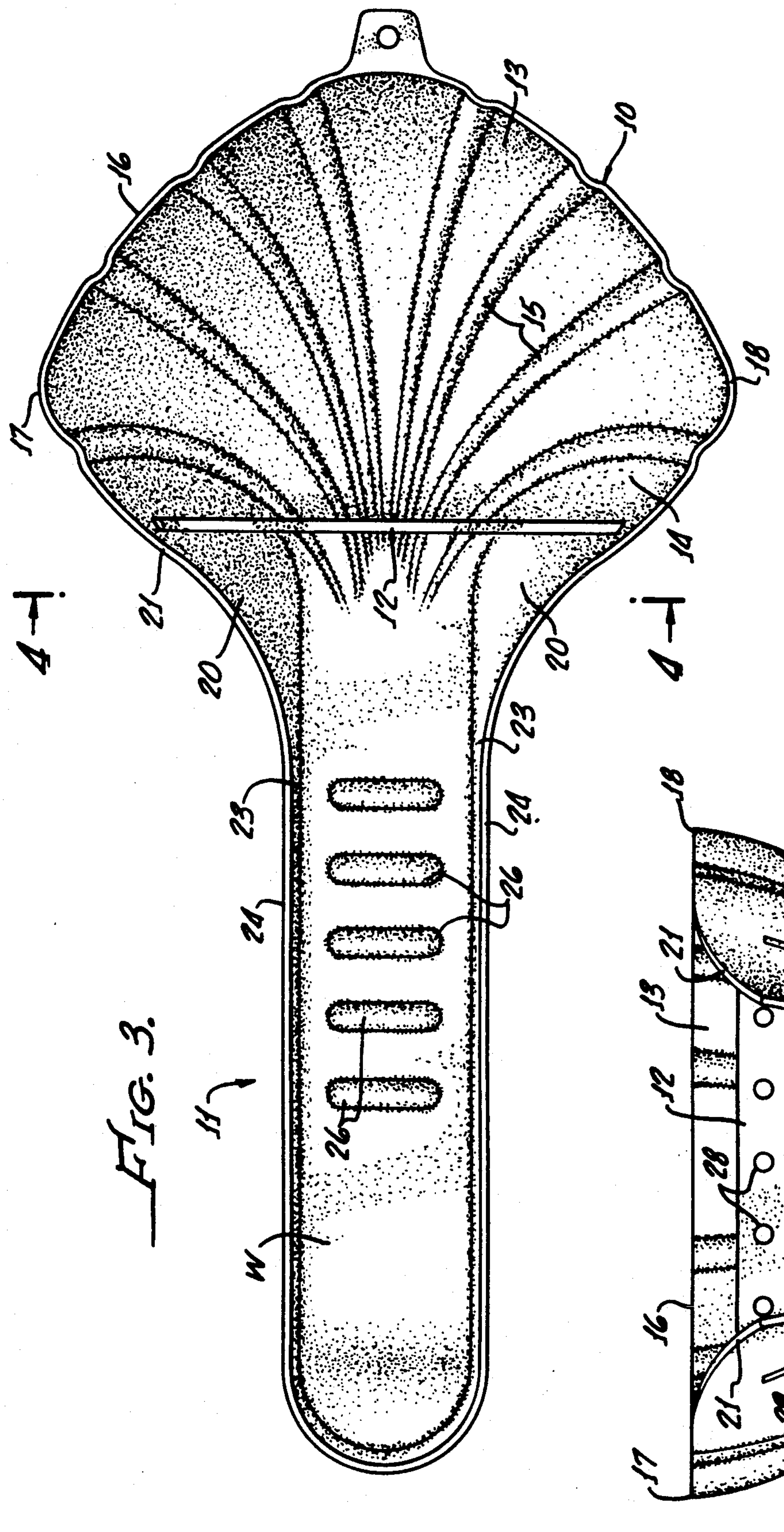
FIG. 3 is a top plan view thereof.

Referring to the drawings, the apparatus comprises wall means to define an open-topped vessel, bowl or dish 10 adapted to deliver water into an open-topped channel or conduit 11, the latter being adapted to conduct water from the vessel to the genitals and perineum. Dam means 12 are provided between the main portion of vessel 10 and conduit 11 to control the velocity of flow through the latter. The dam means further provides a positioning or locating function as set forth below. Further, it prevents painful splashing.

Proceeding to a detailed description of the best mode now contemplated by the inventor, the vessel 10 has an outer portion 13 and an inner portion 14. Outer portion 13 is shown as being shaped generally as a shell, having a rounded lower-outer wall and convergent or fan-like ridges 15 that converge toward channel 11; however, the shell shape is for reasons of identification and aesthetics as distinguished from function. The outer portion 13 could also have many other shapes, including (for example) square. The upper edge 16 of outer portion 13 lies in a single plane that is preferably generally horizontal when the apparatus is used by a person standing in a shower.

The outer portion 13, and the entire apparatus, is preferably formed of synthetic resin. It may be vacuum formed or injection molded, and preferably has a wall thickness sufficient to achieve rigidity. Dam means 12, however, may be stamped instead of molded.

As a specific example, the outer portion 13 is about two inches deep at its deepest point. The distance between the most spaced-apart regions 17,18 (FIG. 2) of the vessel is, in the specific example, about six inches.

The inner portion 14 of vessel 10 has side walls 20 that converge towards each other in a direction away from outer portion 13, as shown in FIG. 3. The upper edges 21 of side walls 20 slope downwardly, and are somewhat concave, the downward slopes being in a direction away from outer portion 13. Sidewalls 20 converge downwardly, from upper edges 21, as shown in section in FIG. 4. Such upper edges 21 are shaped to engage and substantially seal against the body of a typical woman in the pubic area.

Referring next to channel or conduit 11, this is coaxial with the vessel 10. It has an elongate horizontal bottom wall W sized to fit between the inner thighs immediately beneath the perineum. The channel or conduit 11 very preferably has side walls at least at the region thereof relative adjacent vessel 10. In the illustrated preferred embodiment, the channel or conduit has side walls 23 that merge with side walls 20 of dish portion 13. Further, the channel sidewalls 23 have upper edges 24 that form continuations of upper edges 21 of side walls 20, sloping downwardly away from the vessel until the slope becomes progressively less as the distal end of channel or conduit 11 is approached.

In the illustrated preferred embodiment, the sidewalls 23 of the channel or conduit have relatively small vertical dimensions, especially from generally the midpoint of the channel to the distal end thereof. It is possible, but not preferred, to have a conduit that does not have sidewalls. In such a construction, the edges of the conduit would engage the inner thighs so that the inner thighs at regions above the conduit would serve a sidewalls preventing downflow of water.

Protuberances 26 are provided in spaced relationship from each other, on the bottom wall W of and transversely of channel or conduit 11, for the purpose of causing a moderate amount of upward and downward movement of the water moving along such bottom wall. The resulting ripple flow of water enhances cleansing without causing pain or effecting substantial flow of water into the vagina.

The distal end of channel or conduit 11 is bent downwardly, as shown in FIG. 1, to facilitate outflow of water from such channel.

Referring next to dam and positioning means 12, this is mounted (or integrally molded) in the inner portion 14 of vessel 10, generally midway between the widest part of outer portion 13 and the proximal end of conduit 11. Stated otherwise, the dam and positioning means 12 is mounted transversely of the vessel inner portion 14, where the sidewalls 20 of such portion converge towards each other.

Figure 4:
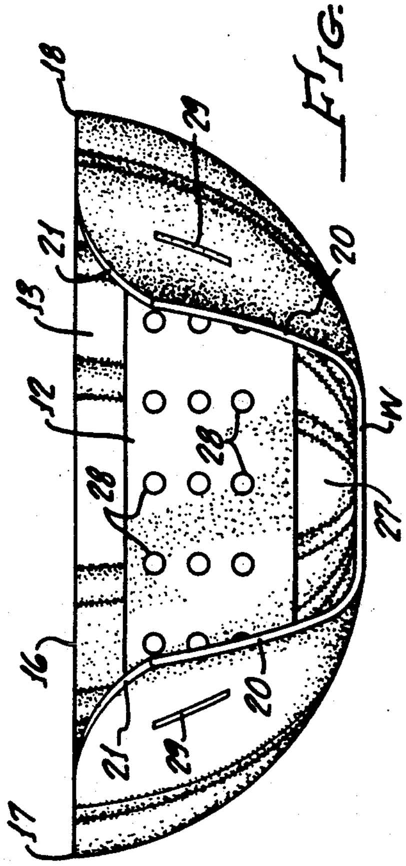
FIG. 4 is a vertical section on line 4—4 of FIG. 3.

There is a relatively large opening, numbered 27, beneath the horizontal lower edge of dam and positioning means 12. Furthermore, there are a multiplicity of holes 28 through such means 12 as shown in FIG. 4. At its end edges, there are ears 29 on the means 12 and which fit into corresponding openings in sidewalls 20 so as to effectively hold the dam and positioning means in the illustrated location, such location being in a generally vertical plane that is perpendicular to the longitudinal axis of the apparatus.

The dam and positioning means 12 is formed of a suitable synthetic resin that will flex sufficiently to permit the ears 29 to be introduced into their openings during assembly It is to be noted that this is the only assembly operation required, and that even this assembly operation may be eliminated by molding (or other) techniques.

In the above-stated specific example, the vertical dimension of lower opening 27 is slightly less than one-half inch. The vertical dimension of dam and positioning means 12 is about one and one-quarter inch, and the diameter of each hole 28 is approximately three-sixteenth inch. The distance from dam and positioning means 12 to the distal end of the conduit or channel 11 is, in the stated specific example, eight inches. The distance between the upper edges of sidewalls 24 ranges between about two inches and about one and three-quarters inches, with the two inch dimension being adjacent vessel 10. In the specific example, the height of sidewalls 23 at the distal end of the conduit or channel is about one-eighth inch; whereas at the proximal end thereof such height is about seven-eighth inch.

It is pointed out that the apparatus could be thin walled and disposable. It may be made sufficiently flexible to conform to the contours of the body, while still having sufficient rigidity to prevent collapse under the weight of water. It may be part of a kit which the new mother brings home from the hospital. It is to be understood that the above-stated examples are exemplary; the device may come in different sizes although it is the belief of applicant that one size will be satisfactory for the great majority of mothers or patients.

DESCRIPTION OF METHODS

The method has been described generally above. The preferred method will now be described in detail. Additional methods will also be described.

The method will be described, for simplicity of description, with reference to the above-disclosed apparatus. However, it is to be understood that different apparatus may be employed and still be within the scope of appended claims.

The method has the great advantage of being extremely simple to perform, and of using economical, simple and easily sanitized (or even disposable) apparatus.

The new mother or other person takes the apparatus into a shower stall, or shower above a bathtub, and introduces the channel or conduit 12 between her inner thighs close to the perineum. The dam and positioning means 12 is caused to be adjacent and preferably engaged with the pubic bone area, and upper edges 21 and 24 are caused to be engaged with the pubic area and inner thighs.

The mother or other person stands in the shower and causes water from the shower head to enter the vessel 10 in one or both of the following two ways: (a) causing (as shown in FIG. 1) the shower spray to strike the front of her torso and then run down her torso into the vessel 10, and (b) directing the shower through the air into the vessel 10 at the region thereof outwardly of the dam and positioning means 12. The vessel becomes partly or completely full, depending upon flow volume and other factors. Water from the vessel portion outwardly of the dam and positioning means 12 flows through the lower opening 27, through holes 28, and to some extent (in some instances) above the dam.

The dam and positioning means 12 substantially prevents shower water from splashing against the new mother and causing pain. Instead, there is a flow of water from the vessel 10 below and to some extent through the dam and positioning means, such water flowing front-to-back past the labia majora and minora, the vulva, the perineum and the anus. The front-to-back flow prevents any possibility of contamination of the genital regions, or the wound, by the water.

The new mother or other person may stand in the shower as long as desired. To prevent wastage of water, the shower flow volume may be caused to be quite low yet sufficient to achieve not only a cleansing but a soaking or sitz-bath action relative to episiotomy stitches. Very preferably, the water is caused to be quite warm so as to stimulate blood flow and promote healing of the tissues In accordance with one aspect of the method, the amount of water received by the vessel 10 is increased by moving the arms of the mother or other person adjacent the body in V-relationship, so that the maximum amount of water flows down the torso and arms, and converges into the vessel. The sides of both hands are held adjacent opposite sides of the vessel. Otherwise, only one hand is employed to hold the vessel.

ADDITIONAL METHODS

The above described apparatus is also highly useful in methods distinctly different from those described above, and relating to the treatment of genital infections (such as yeast infections), and in the care of geriatric patients.

The method is as follows. The person or patient sits on a toilet (water closet), and causes the channel or conduit means 11 to be adjacent the perineum, and the dam and positioning means 12 to be adjacent and preferably in contact with the pubic bone area. Then, water is poured (for example, from a pitcher) into vessel 10 at regions outwardly of dam 12, at a sufficient rate that the water flows beneath the dam and front-to-back adjacent the areas to be treated and/or cleansed.

The water may be caused to have appropriate prescribed medicines therein, it being understood that the word "water" as here employed includes also other liquids for medicinal and/or cleansing purposes.

The water upon reaching the distal portion of the conduit or channel means flows into the water already present in the toilet bowl.

After use, the apparatus is readily sanitized because of its relatively small size and simple construction.

For geriatric patients who are not in full possession of their mental or physical facilities, for example patients with relatively advanced Alzheimer's disease, the method is of course performed by an attendant or nurse relative to the patient, instead of being performed by the patient.

The foregoing detailed description is to be clearly understood as given by way of illustration and example only, the spirit and scope of this invention being limited solely by the appended claims.

What is claimed is:

1. Apparatus for bathing, treating or soaking the perineum of a woman, comprising;

(a) an open channel or conduit shaped and sized to fit between the inner thighs of a woman in proximity to the perineum of said woman.

(b) a vessel connected to one end of said channel or conduit and communicating therewith the delivery of water thereto, said vessel being shaped and sized to be adjacent the lower torso of said woman when said channel or conduit is between the inner thighs of said woman in proximity to the perineum thereof, and (c) dam means provided generally in said vessel relatively adjacent said channel or conduit, to prevent splashing of shower water against said woman and to reduce the flow velocity of water in said channel or conduit, (d) characterized that said channel or conduit and said vessel are so related that, when said channel or conduit is between the inner thighs of said woman and adjacent the perineum thereof, and when said vessel is adjacent said lower torso thereof, when water is introduced into said vessel it will flow out thereof into said channel or conduit, and past and in contact with said perineum for healing, soaking, cleansing or treating the same.

2. The invention as claimed in claim 1, in which said dam means are so located that when engaged by the pubic bone area of said woman the apparatus will have been inserted by the correct amount, so that said dam means is also a positioning means.

3. The invention as claimed in claim 1, in which said dam means has an opening therebeneath through which water may flow from said vessel to said channel or conduit.

4. The invention as claimed in claim 1, in which said dam means has flow openings therethrough.

5. A method of cleansing and soaking the perineum regions of women, said method comprising:

(a) providing a substantially open-topped vessel having elongate substantially open-topped water-conducting means extending from said vessel and communicating therewith, such water-conducting means being narrow so as to be comfortably insertable between the upper-inner thighs of a woman standing in a shower bath, (b) inserting said water-conducting means between said upper-inner thighs of a woman at such elevation and in such relationship that water flowing along said water-conducting means will engage the perineum regions of said woman, while orienting said vessel with its open top upward, and (c) directing water from a shower bath head into said vessel through the open top thereof so that said water then flows out of said vessel along said water-conducting means and along the perineum regions, said directing and flow being effected while said woman is standing in a shower.

6. The invention as claimed in claim 5, in which said direction is effected by causing at least a large proportion of water spray from said head to strike the torso of said woman and then flow down said torso into said vessel.

7. The invention as claimed in claim 5, in which said directing is effected by causing at least a portion of water spray from said head to pass directly through the air into said vessel.

8. The invention as claimed in claim 5, in which said directing is effected by causing at least a portion of water spray from said head to strike the torso of said woman and then flow down said torso into said vessel, and in which said directing is effected by causing at least a proportion of water spray from said head to pass directly through the air into said vessel.

9. The invention as claimed in claim 5, in which said vessel is disposed in front of the pubic region of said woman, and in which said method further comprises causing said open-topped water-conducting means to pass water from said vessel adjacent and in contact with the labia of said woman.

10. The invention as claimed in claim 9, in which said woman is a postpartum vaginal delivery mother having episiotomy stitches, and in which said method is performed for such a time period and with such a water temperature as to soak said stitches, and afford some relief from the pain and discomfort thereof.

11. The invention as claimed in claim 10, in which said method further comprises reducing the rate of flow along said water conducting means to prevent water from passing through the cervix.

12. The invention as claimed in claim 10, in which said method comprises preventing water from splashing from said vessel against the genitals.

13. The invention as claimed in claim 9, in which said method further comprises providing positioning means in said vessel and bringing said positioning means into contact with the pubic bone area to thereby locate said vessel and water conducting means properly.

14. The invention as claimed in claim 9, in which said method further comprises providing contoured edge regions at the junction regions between said vessel and water-conducting means, and causing said edge regions to engage said woman and generally seal against her skin to thus minimize loss of water.

* * * * *